(12) United States Patent
Hubbard

(10) Patent No.: US 6,900,445 B2
(45) Date of Patent: May 31, 2005

(54) IRRADIATION APPARATUS

(75) Inventor: Neil Trevor Hubbard, Worsthorne (GB)

(73) Assignee: Ingleby (1472) Limited, High Wycombe (GB)

(*) Notice: Subject to any disclaimer, the term of this patent is extended or adjusted under 35 U.S.C. 154(b) by 136 days.

(21) Appl. No.: 09/798,262

(22) Filed: Mar. 2, 2001

(65) Prior Publication Data

US 2001/0028041 A1 Oct. 11, 2001

(30) Foreign Application Priority Data

Mar. 3, 2000 (GB) ............................................... 0005118

(51) Int. Cl.[7] .............................. A61N 5/00; G21G 5/00
(52) U.S. Cl. .............................. 250/492.1; 250/492.2; 250/442.11
(58) Field of Search .......................... 250/492.1, 492.2, 250/442.11, 308; 378/68; 359/216

(56) References Cited

U.S. PATENT DOCUMENTS

| 3,642,400 | A | * | 2/1972 | Theodorsen |
| 3,655,468 | A | * | 4/1972 | Bastone et al. ............ 156/62.2 |
| 4,029,967 | A | * | 6/1977 | Tetzlaff ........................ 378/69 |
| 4,066,907 | A | * | 1/1978 | Tetzlaff ........................ 378/69 |
| 5,001,352 | A | * | 3/1991 | Tetzlaff ................. 250/453.11 |
| 5,090,350 | A | * | 2/1992 | Hammond et al. ........... 118/50 |
| 5,177,632 | A | | 1/1993 | Schwartz et al. |
| 5,390,481 | A | * | 2/1995 | Langner |
| 5,712,894 | A | | 1/1998 | Lanotte |

FOREIGN PATENT DOCUMENTS

| EP | 0 374 068 A1 | | 6/1990 | |
| GB | 0105580 | * | 4/1984 | ............ G21K/1/08 |

* cited by examiner

Primary Examiner—Nikita Wells
Assistant Examiner—Anthony Quash
(74) Attorney, Agent, or Firm—Beyer Weaver & Thomas LLP

(57) ABSTRACT

Polymeric article irradiation apparatus comprising a radiation source and a carousel, the carousel including drive means and a plurality of carriers for polymeric articles, each carrier being mounted on the carousel and adapted to rotate about a respective axis, wherein the drive means is adapted to cause the carousel to rotate about a central axis in use and further adapted to cause each carrier to rotate about said respective axis during rotation of the carousel about said central axis.

17 Claims, 3 Drawing Sheets

IRRADIATION APPARATUS

FIELD OF THE INVENTION

This invention relates to apparatus for irradiation of articles, particularly but not exclusively for irradiation sterilisation, cross-linking or modification of articles composed of polymeric materials.

BACKGROUND OF THE INVENTION

Existing apparatus for sterilisation of polymeric articles suffer from various problems. In one form of previously known apparatus, polymeric articles are placed in bins on a conveyor which moves in a rectangular path around the radiation source. The articles, for example moulded polymeric products receive different doses of radiation dependent on their position within each bin. Articles in the middle of each bin are shielded by other articles. This may be of little importance in bulk sterilisation of non-organic materials but the effect on organic materials such as polymers is very dose dependent. Since the conveyor speed is set to give a specific dose, it is impossible to provide non-standard doses without modification of the plant which is usually used simultaneously for other purposes. It has also been common to use a turntable located in front of a radiation source. However articles in inner layers may be shielded by those in the outer layers. Because the available area for the turntable is finite, the quantity of articles which may receive even treatment is limited by the outside diameter of the turntable.

SUMMARY OF THE INVENTION

According to the present invention polymeric article irradiation apparatus comprises a radiation source and a carousel, the carousel including drive means and a plurality of carriers for polymeric articles, each carrier being mounted on the carousel and adapted to rotate about a respective axis, wherein the drive means is adapted to cause the carousel to rotate about a central axis in use and further adapted to cause each carrier to rotate about said respective axis during rotation of the carousel about said central axis. Preferred apparatus provides a planetary motion to each carrier. Each carrier periphery follows an epicyclic path during rotation about the central axis. Accordingly each article mounted within a carrier also follows an epicyclic path arranged so that each article receives the same exposure to the radiation source. The articles may be exposed to the radiation source for a period of time necessary to achieve the irradiation dosage in accordance with conventional practice. The central and carrier axes are usually disposed vertically. In a preferred apparatus the carousel may rotate at 5 rpm and the carriers may rotate at 6 rpm. Alternative rotational speeds may be employed as desired to ensure that the articles receive even irradiation during the period of exposure to the source. The drive means may conveniently comprise an electric motor coupled to the central shaft of the carousel. The carriers may be connected to the central shaft by means of a chain and sprocket arrangement to one carrier, the remaining carriers being connected by a circumferential chain drive engaging sprockets on each carrier. Any convenient number of carriers may be provided, for example 6 to 8, preferably 7. Each carrier may include a platform adapted to support a bin or other container for polymeric articles. Two bins may be located one above the other on each platform, permitting the bins to be interchanged when a half of a full radiation dose has been applied. This reduces or eliminates any tendency for upper and lower ends of articles within each bin to receive reduced radiation doses. The articles should be preferably arranged around the periphery of each bin. The apparatus of the present invention increases the quantity of polymeric products which can be evenly treated to a close tolerance of radiation dose from a given floor area.

BRIEF DESCRIPTION OF THE DRAWINGS

The invention is further described by means of example but not in any limitative sense with reference to the accompanying drawings of which.

DETAILED DESCRIPTION OF THE INVENTION

Figure 1:
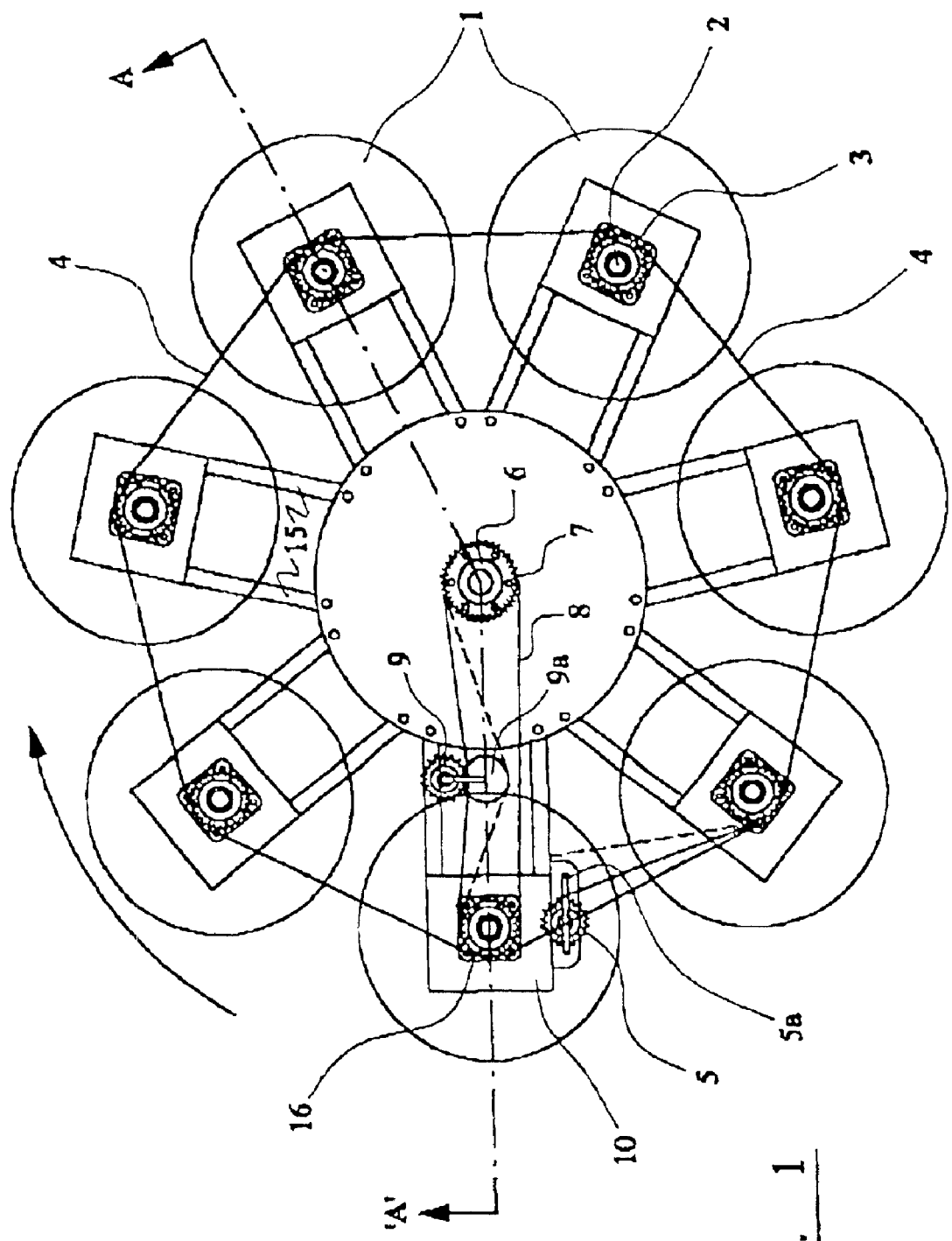
FIG. 1 is a plan view of apparatus in accordance with the invention.
Figure 2:
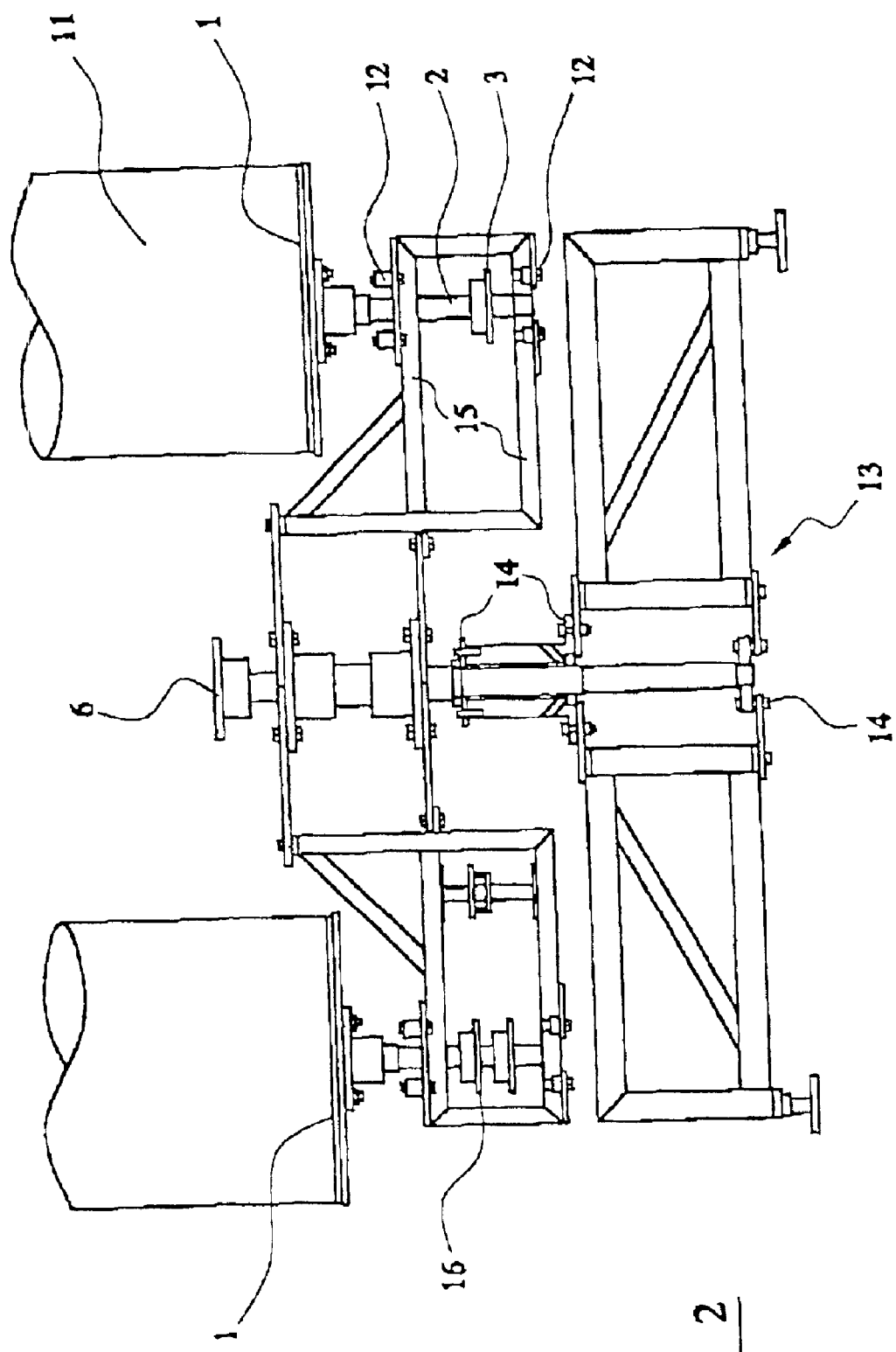
FIG. 2 is a section of A—A of FIG. 1.
Figure 3:
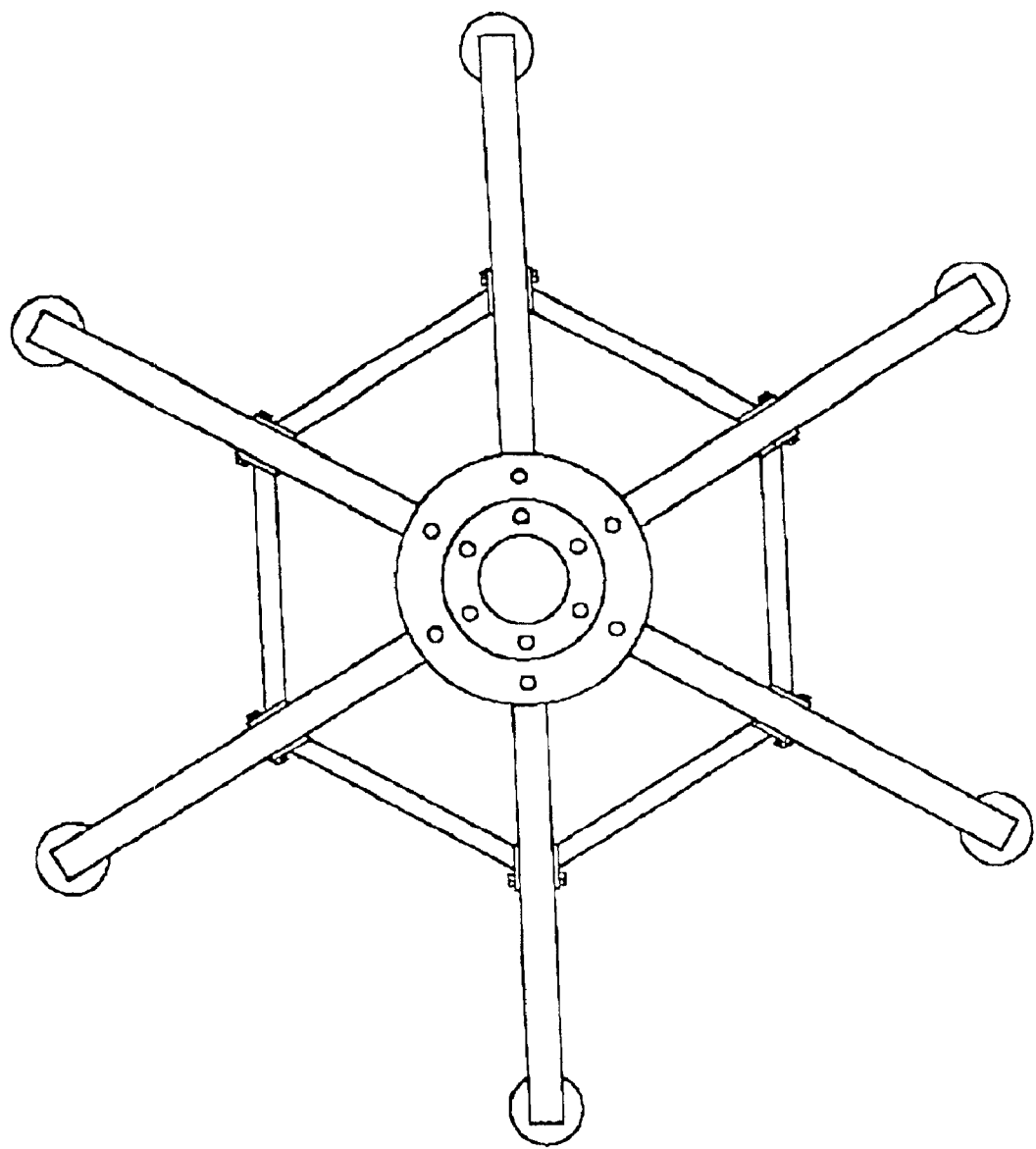
FIG. 3 is a plan view of the base of the apparatus.

The apparatus shown in the drawings comprises carriers 1 providing horizontal platforms upon which containers 11 of polymeric articles may be disposed. Each carrier 1 is mounted for rotation on a respective axle 2 mounted in a bearing 12 driven by a sprocket 3. Seven carriers are shown although an alternative number may be used as convenient. A carousel comprising ground engaging base portion 13 is shown generally in FIGS. 2 and 3. A central shaft 6 mounted for rotational movement in bearings 14 and rotatable arms 15 supporting the bearings 12 and the carriers mounted on them. A motor (not shown) connected to the central shaft 6 causes rotation of the arms 15. A sprocket 7 and chain 8 connected to a sprocket 16 on one carrier are arranged to cause the carrier to rotate at 6 rpm as the carousel is driven at 5 rpm by the motor. The remaining carriers connected by a circumferential chain 4 and respective sprockets 3. Adjustable tensioning sprockets 5 and 9 may be moved to positions 5a and 9a to take up slack in the drive chains.

In use the apparatus may be disposed within a radiation chamber at an appropriate distance of eg 2 to 3 meters from the source. Each polymeric article within a bin 11 follows an epicyclic path due to the planetary motion of the carriers 1.

The apparatus of the present invention maximises the quantity of products which can be evenly treated to a close dosage tolerance within a limited floor area.

Given a floor area of 1.525 m, the maximum number of rods of 75 mm diameter×0.5 m (about 2 kg in weight) that will fit within the circumferenece in a single layer with 3 mm separation is 57, using the planetary turntable in the same space it is 77. In practice, because of the manual handling problem in carrying materials into the inside of the plant, the maximum turntable treated quantity was restricted to a single bin of <15. Using the planetary system, the individual bins can be reloaded and then quickly exchanged. At a quoted plant cost of £600 per hour downtime this is very cost effective. A further refinement has been to place 2 bins on each station so that at half dose time, they can be exchanged top to bottom and thereby effectively remove the end effect. This was previously possible only with <15 size. It would clearly be impractical (at 10/min) to manually exchange rods in a 1.5 m bin set.

Given the above it is now possible to process 144 at 2 kg=288 kg instead of 30 at 2 kg=60 kg in one run and with an even dose distribution.

I claim:

1. An apparatus to cross link polymeric materials, the apparatus comprising:

a carousel, the carousel including a drive mechanism and a plurality of carriers configured to carry polymeric articles, each carrier being mounted on the carousel and adapted to rotate about a respective axis, the drive mechanism being adapted to cause the carousel to continuously rotate about a central axis and further adapted to cause each carrier to rotate about said respective axis during rotation of the carousel about said central axis so that each carrier follows an epicyclic path during rotation about the central; and a radiation source mounted in a fixed position relative to the carousel such that the radiation source is equidistant from the plurality carriers so that the polymeric articles in the plurality of carriers each receive a substantially equal amount of radiation from the radiation source, the radiation source further configured to simultaneously deliver a substantially equal radiation dosage to the polymeric articles sufficient to cause cross-linking of the articles during the rotation of the carriers rotating around their respective axes during the continuous rotation of the carousel around the central axis.

2. Apparatus as claimed in claim 1, wherein as each carrier follows the epicyclic path during rotation about the central axis, the polymeric articles in each carrier receive substantially the same amount of exposure from the radiation source.

3. Apparatus as claimed in claim 1, wherein the central and carrier axes are vertical.

4. Apparatus as claimed in claim 1, wherein the carousel rotates at 5 rpm and the carriers rotate at 6 rpm.

5. Apparatus as claimed in claim 1, wherein the carriers are connected to the central shaft by means of a chain and sprocket arrangement to one carrier, the remaining carriers being connected by a circumferential chain drive engaging sprockets on each carrier.

6. Apparatus as claimed in claim 1, including 6 to 8 carriers.

7. Apparatus of claim 1, wherein each carrier includes a platform adapted to support a container for polymeric articles.

8. Apparatus as claimed in claim 7, wherein the container comprises a bin.

9. Apparatus as claimed in claim 8, wherein two bins are located one above the other on each platform.

10. An apparatus, comprising:

a carousel configured to rotate about a first axis;

a plurality of carriers mounted to the carousel, each of the carriers configured to rotate about a plurality of second axes parallel to the first axis; and a drive mechanism coupled to the carousel and the plurality of carriers, the drive mechanism configured to cause the carousel to continuously rotate in a first direction about the first axis and the plurality of carriers to each rotate in a second direction about the second axes respectively, such that the carriers travel a substantially epicyclic path; and a radiation source mounted in a fixed position relative to the carousel such that the radiation source is equidistant from the plurality carriers so that the polymeric articles in the plurality of carriers each receive a substantially equal amount of radiation from the radiation source when the carousel and the plurality of carriers are rotating about their first axis and second axis respectively, the radiation source further configured to simultaneously deliver a substantially even radiation dosage to the polymeric articles sufficient to cause cross-linking.

11. The apparatus of claim 10, wherein the drive mechanism is configured to rotate each of the plurality of carriers mounted to the carousel at substantially the same rotational rate.

12. The apparatus of claim 11, wherein the drive mechanism comprises a first chain and sprocket arrangement configured to rotate a selected first carrier among the plurality of carriers and a circumferential chain drive engaging carrier sprockets on each of the remaining carriers respectively.

13. The apparatus of claim 10, wherein each of the plurality of carriers is configured to carry polymeric articles, wherein the polymeric articles are exposed to substantially the same amount of radiation from the radiation source as the carriers travel the substantially epicyclic path.

14. The apparatus of claim 10, wherein the carriers comprise bins respectively.

15. The apparatus of claim 10, wherein the plurality of carriers ranges from 6 to 8 carriers.

16. The apparatus of claim 10, wherein the carousel rotates at approximately 5 rpms and the plurality of carriers rotate at approximately 6 rpms.

17. The apparatus of claim 10, wherein the first axis and the plurality of second axes are substantially vertical.

* * * * *